United States Patent
Jervis et al.

(10) Patent No.: US 7,914,435 B2
(45) Date of Patent: Mar. 29, 2011

(54) EVERTING GYNECOLOGICAL BRACHYTHERAPY APPLICATOR AND METHOD

(75) Inventors: James E. Jervis, Atherton, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 505 days.

(21) Appl. No.: 11/811,295

(22) Filed: Jun. 7, 2007

(65) Prior Publication Data
US 2008/0306323 A1 Dec. 11, 2008

(51) Int. Cl.
*A61N 5/00* (2006.01)
(52) U.S. Cl. .......................................................... 600/6
(58) Field of Classification Search .................. 600/1–8; 606/191
See application file for complete search history.

(56) References Cited

U.S. PATENT DOCUMENTS

| | | | |
|---|---|---|---|
| 3,872,856 A | 3/1975 | Clayton | |
| 4,324,262 A | 4/1982 | Hall | |
| 4,554,909 A | 11/1985 | Pino y Torres | |
| 4,871,358 A | 10/1989 | Gold | |
| 4,946,440 A | 8/1990 | Hall | |
| 5,002,557 A * | 3/1991 | Hasson | 606/191 |
| 5,070,597 A | 12/1991 | Holt et al. | |
| 5,653,683 A | 8/1997 | D'Andrea | |
| 5,720,717 A | 2/1998 | D'Andrea | |
| 5,947,891 A | 9/1999 | Morrison | |
| 6,231,544 B1 * | 5/2001 | Tsugita et al. | 604/104 |
| 6,390,968 B1 | 5/2002 | Harmon | |
| 6,641,518 B2 | 11/2003 | Wolfson et al. | |
| 2003/0153803 A1 | 8/2003 | Harmon | |
| 2006/0173235 A1 * | 8/2006 | Lim et al. | 600/6 |

* cited by examiner

*Primary Examiner* — Charles A Marmor, II
*Assistant Examiner* — Christine D Hopkins
(74) *Attorney, Agent, or Firm* — Thomas M. Freiburger

(57) ABSTRACT

An everting applicator for brachytherapy of body cavities such as the vagina has a flexible sleeve secured to a distal mandrel, both the sleeve and the mandrel having internal lumens. The flexible sleeve has a diverging opening at its distal end, preferably bell-shaped or cone-shaped, such that when the open end is pushed against the mouth of a vagina, the sleeve will evert back upon itself, progressively unrolling to an inside out configuration wherein, fully inserted, the sleeve is fully everted back over the exterior surface of the mandrel. A radiation source, isotopic or electronic, is then inserted into the mandrel lumen to commence a therapeutic irradiation procedure of tissues of the vagina.

13 Claims, 9 Drawing Sheets

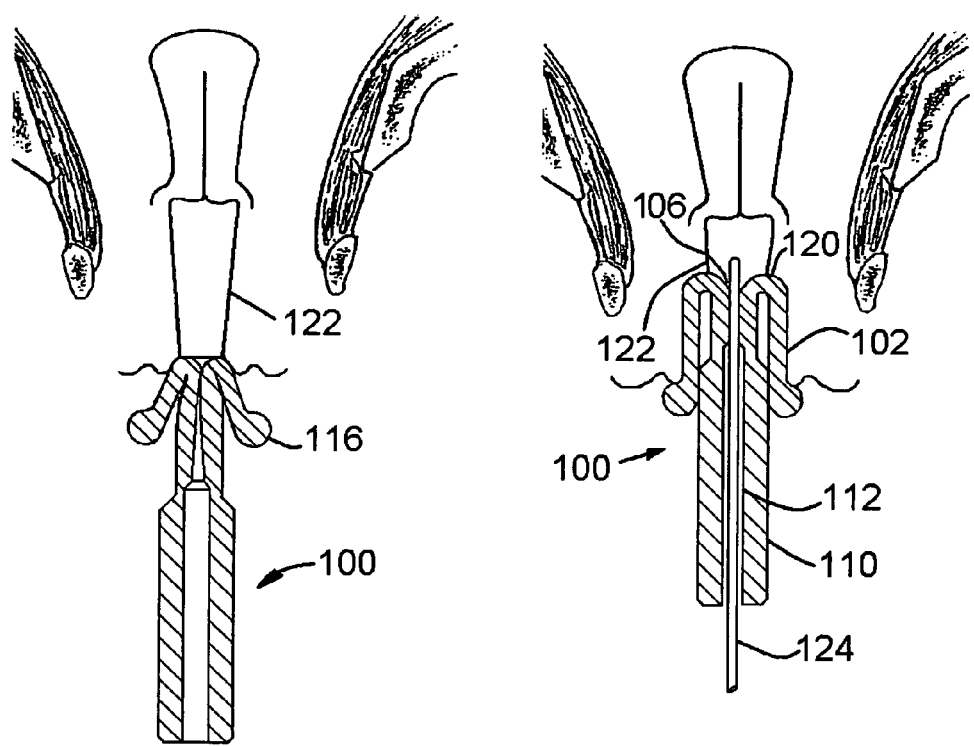

EVERTING GYNECOLOGICAL BRACHYTHERAPY APPLICATOR AND METHOD

BACKGROUND OF THE INVENTION

This invention concerns radiation therapy, especially brachytherapy, for treating tissues which may have diffuse proliferative disease. In brachytherapy, the radiation source is generally placed within a surgically created or naturally occurring cavity in the body. In particular, this invention relates to an applicator for delivering radiation therapy to a vaginal cavity and/or to adjacent tissue, often following surgical treatment of cancer. Radiation therapy of this sort is generally administered over a period of time in partial doses, or fractions, the sum of which comprises a total prescribed dose. This fractional application takes advantage of cell recovery differences between normal and cancerous tissue whereby normal tissue tends to recover between fractions, while cancerous tissue tends not to recover.

In brachytherapy, a prescribed dose is selected by the therapist to be administered to a volume of tissue (the target tissue) lying outside the treatment cavity into which the radiation source will be placed. Generally the prescribed dose will include a minimum dose to be delivered at a preferred depth outside the treatment cavity (the prescription depth). Since, in accordance with the laws of physics, radiation intensity falls off with increasing distance from the radiation source, it is desirable to create and maintain a space between the source of radiation and the first tissue surface to be treated (generally the cavity wall since the source is placed within the cavity) in order to moderate the absorbed dose at the cavity surface. Although not always the case, generally the absorbed dose at the prescription depth outside the cavity is to be uniform. In this isotropic case, it is therefore important that the incident radiation on the interior surface of the cavity be the same at all points being treated. To accomplish this objective, it may be necessary to sequentially position a single radiation source through a series of positions (or utilize multiple sources strategically placed) which, in the aggregate, produce a uniform absorbed dose incident on the cavity surface being treated. When this is achieved, the absorbed dose reaching into tissue will be the same at all points being treated, and the minimum prescribed dose can be delivered at the prescription depth as nearly as the treatment plan will allow. Furthermore, by selecting the radiation source intensity (radioisotope emissions or x-ray tube output) and controlling treatment time and the distance from the source(s) to the cavity interior surface, the incident radiation can be sufficiently moderated to avoid substantial damage to normal tissue.

Rigid applicator cylinders designed to receive radioisotopes have traditionally been used to treat vaginal cancer or malignancies in adjacent tissues. A principal function of an applicator is to establish and maintain distance relationships between the radiation source and the tissues being treated such that the prescribed dose is delivered to a desired prescribed depth of tissue, and yet normal tissues nearest the radiation source are not subjected to absorbed doses sufficient to risk significant necrosis. Applicators of this general type are available, for example, from Varian Medical Systems, Inc., Charlottesville, Va. Such prior art applicator cylinders are sized to the vaginal cavity or adjacent anatomy, but because the tissues should be positioned closely against the exterior surface of the applicator, large applicators must be chosen that are often painful on insertion, and once inserted may fail to provide a good fit. Additionally, prior art cylinders are generally straight, with a central lumen into which radioactive seeds are delivered and later removed after completion of prescribed therapy. As a result, anisotropic treatment plans are difficult to achieve with such symmetrical applicators. Thus conventional applicators are less than ideal in many cases.

SUMMARY OF THE INVENTION

Although this invention is disclosed with specific reference to therapeutic application of radiation within the vagina, the principles of the invention may be similarly applied to other brachytherapy situations in other natural or surgically created anatomic spaces, or to therapeutic situations other than post-surgical treatment of cancer, and still fall within the bounds of this invention. The term "proximal" as used herein refers to the end of the element being described which is nearest the therapist when in use, while the term "distal" refers to the end farthest from the therapist, and which is generally inserted into the patient.

The applicator of this invention comprises a polymeric sleeve exhibiting substantially elastomeric behavior, particularly diametrally, an end of which sleeve can be turned inside-out on itself along at least part of its length. The opposite end of the sleeve can be fastened to, or is monolithic with one end of a substantially rigid or semi-rigid, cylindrical, tubular mandrel which extends axially away from the sleeve. The open end of the sleeve (opposite the mandrel) further comprises a diametral transition section terminating in a cuff or handle, the outer diameter of which is larger than the vaginal opening of the patient in order to prevent entry of the applicator cuff into the vagina. When the cuff and attached everted portion of the sleeve are restrained axially relative to the mandrel and the mandrel is advanced through the cuff, the body of the sleeve progressively everts until the inner surface of the sleeve becomes the new outer surface of the applicator. The mandrel further comprises an axial lumen sized to accommodate a radiation source (and source catheter if any), said source extending at least from the end of the mandrel opposite the end connected to the sleeve for a length sufficient to allow positioning of the radiation source for delivery of the prescribed therapy. Beyond this length, the lumen may extend to join that of the sleeve, or may have a closed distal end.

Preparatory to use, the cuff and transition section are turned inside-out, such that the doubled-over wall of the sleeve at the transition section becomes the distal end of the applicator. The exterior diameter of the doubled-over portion of the wall should be sized to enter comfortably into the vagina. If desired, all or a portion of the sleeve wall may be contoured or of foamed material for patient comfort, but also to shape the vaginal cavity when the applicator is properly positioned within the vagina. In combination with the wall thickness of the sleeve, the mandrel should be sized to expand the outer portion of the doubled over wall to stretch the vagina to the desired contour. As the mandrel is advanced and the cuff is restrained, the sleeve progressively everts until both the (at least) distal portion of the mandrel as well as the inside-out sleeve are positioned within the now distended vagina. The length of the everted applicator sleeve must be adequate to reach the full vaginal depth if that is required for proper delivery of the prescribed dose of radiation. If necessary to facilitate sleeve eversion and dilation of the vagina, lubrication may be applied between the inner and outer portions of the doubled over wall of the sleeve to provide for sliding of the wall portions and the exterior surface of the mandrel, and preferably between the outer sleeve wall and the vaginal wall as well to eliminate any adhesion or friction which might prove uncomfortable. Longitudinal fiber reinforcement may be built into the wall of the sleeve such that advancing the mandrel during eversion against the axial resistance of the cuff or handle results in an increased diameter rather than in any substantial stretching of the sleeve length.

Once the applicator is positioned within the vagina, a radiation source may be introduced into the mandrel lumen and radiotherapy commenced. If an x-ray source is used, for example a source as described in U.S. Pat. No. 6,319,188, the source may be manipulated through use of a catheter. If an isotope source is used, it may be mounted on a wire as is conventional, and used with an afterloader, for example a GAMMAMED afterloader (Varian Medical Systems, Inc., Charlottesville, Va.). Other source handling methods are known to those of skill in the art and may also be employed.

Several alternate features are contemplated and result in different embodiments, all of which are within the scope of the invention. As mentioned above, the structure of the applicator may comprise an open or "through" (rather than a closed) mandrel lumen communicating with the lumen of the sleeve, with the sleeve proximal end joined to the mandrel by bonding or mechanical fixation using conventional methods. In another embodiment, the through mandrel lumen may be sized or used for the additional purpose of venting or evacuating the vaginal space as the mandrel is advanced. If the proximal end of the mandrel comprises a conventional hub with a central seal and a secondary access port from outside the patient to the central mandrel lumen is provided, fluids can be withdrawn from the vaginal cavity around the applicator, or therapeutic agents can be administered. Additional lumina may be provided which communicate with other portions of the applicator as necessary to address auxiliary purposes, for example to accommodate wiring for radiation sensors, or to accommodate a plurality of sources or multiple source positions within or on the applicator. Another feature which can be used on the outer (after eversion) sleeve portions of the applicator embodiments presented herein is grooving or texturing, or an open, outer matrix, all suitable for facilitating fluid flow at the vaginal cavity/applicator interface.

The two portions, mandrel and sleeve, may be one monolithic structure but having different geometry and/or physical properties such that functionality of the applicator is accommodated (more rigid mandrel section and elastomeric or resilient sleeve section). For example, the sleeve portion may be of foamed material (such as foamed urethane) in order to offer a degree of radial compliance at the surface of the vaginal cavity, thus providing for accommodation or formation of different surface contours. As a further variation, the outer diameter of the mandrel and/or the wall thickness of the sleeve portion of the applicator may be varied along their/its length such that preferred, potentially non-uniform outer configurations of the applicator can be provided for therapeutic applications requiring non-uniform absorbed radiation dose prescriptions at different locations within the vagina. Alternatively, this radiation variation can be achieved with radiation-absorbing additives to the sleeve or mandrel or coatings at selected locations.

In contrast to traditional cylindrical applicators, the applicators of this invention offer easier insertion before dilation, and eliminate axial friction between the applicator and the vaginal wall as the mandrel advances and the applicator is deployed. By expansion of the applicator in the manner described, frictional drag at the vaginal wall is largely eliminated and dilation of the vagina is gradual, gentle and more comfortable for the patient.

DESCRIPTION OF THE DRAWINGS

FIG. 3 depicts in coronal section view, the applicator introduced into the mouth of the vagina.

FIG. 4 depicts the applicator as in FIG. 3, but with the mandrel advanced partially into the vagina causing partial eversion of the sleeve portion of the applicator. An optional obturator is shown within the applicator lumen to be used if a support guide is necessary as the eversion process progresses.

DESCRIPTION OF PREFERRED EMBODIMENTS

Figure 1:
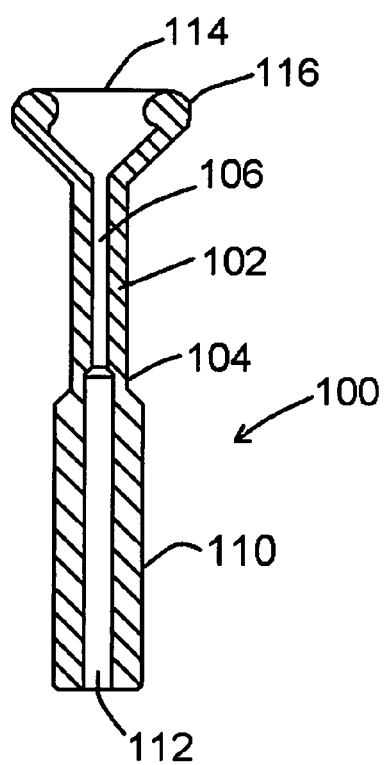
FIG. 1 depicts in longitudinal section view, an applicator embodiment of the invention comprising sleeve and mandrel portions.

FIG. 1 shows an applicator 100 of the present invention, comprising a sleeve portion 102 joined at one end, its proximal end 104, to the distal end of a cylindrical mandrel 110. The mandrel 110 has a central lumen 112 communicating with a central lumen 106 of the sleeve 102. Proximate to the distal end 114 of the sleeve 102, the sleeve increases in diameter to connect with a cuff 116. The diameter of the cuff is sufficiently great that, together with its structural properties (which might be reinforced, for example by a metal or structural polymer ring 117 seen in FIG. 5d), it is prevented from entering the vagina when the applicator 100 is being deployed. If desired, a handle (not shown) can be provided as an alternative to a cuff and the handle will serve equally to prevent entry into the vagina, but will also facilitate manipulation of other elements of the applicator by the therapist during their insertion into the vagina and/or during radiotherapy. Materials of choice for the sleeve 102 must be substantially immune to damage from prescribed radiation, must offer modest elastomeric properties consistent with eversion, and must be amenable to fastening to the mandrel 110 (or offer a range of properties allowing a monolithic structure for the applicator). Suitable materials for the sleeve 102 would include soft silicone elastomers, thermoplastic elastomers like Kraton (Kraton Polymers US, LLC, Houston, Tex.) or thermoplastic rubbers like Santoprene (Exxon Mobil Corp., Akron, Ohio). Mandrel 110 materials should be more robust and would include harder silicone elastomers, polycarbonate, or ethylene-propylene rubber. Harder and softer rubbery materials can be comolded into one integral structure.

Figure 2:
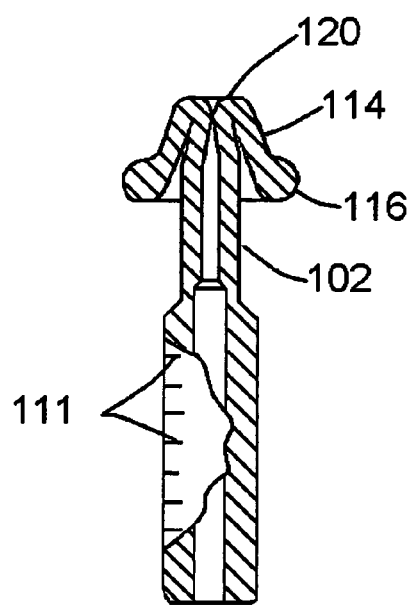
FIG. 2 depicts in section view, the applicator of FIG. 1 with the distal end turned inside-out.

FIG. 2 shows the distal end 114 of the sleeve 102 turned inside out, positioning the cuff 116 adjacent to the cylindrical portion of the sleeve 102, and the tapered section of the distal end 114 of the sleeve 102 forming a new, doubled-over distal extremity 120 of sleeve 102. By controlling the geometry and material properties of the sleeve 102 proximate to the distal end 114, the outer diameter of the distal extremity 120 can be sized for easy insertion into the mouth of the vagina. Positioned as shown in FIG. 3, the applicator will ease gently into the vagina when deployed, and the cuff 116 will serve to anchor what is now the outer portion of the applicator at the mouth of the vagina 122. Along the length of the mandrel 110, depth calibration markings 111 (FIG. 2) can be provided to assist proper depth of insertion of the applicator 100, as is described later herein.

FIG. 4 shows the applicator within the vagina 122 after the mandrel 110 has been advanced into the applicator sleeve 102, continuing eversion of the sleeve and advancing the distal extremity 120 of the applicator 100 within the vagina 122. If support is necessary to prevent buckling of the sleeve 102, or to steer the distal extremity 120 as the mandrel 110 is advanced, an obturator 124 may be manipulated within the lumina 106 and 112 to facilitate insertion of the applicator 100 into the vagina 122. Care must be taken to avoid vaginal injury during manipulation of the obturator. Such an obturator can be made from a structural polymer, for example, polypropylene or polycarbonate.

Figure 5A:
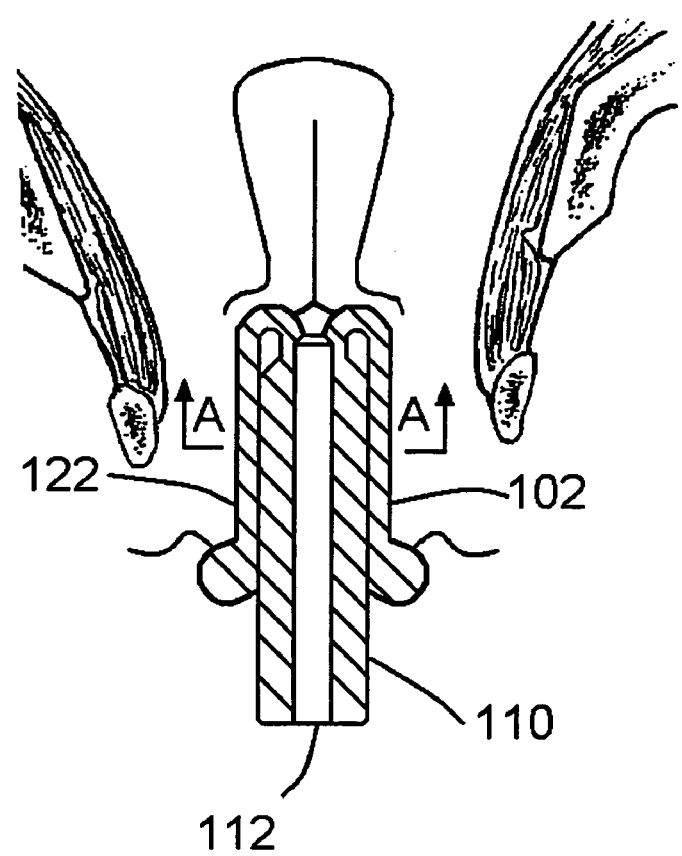
FIG. 5a depicts the applicator as in FIG. 4, but with the mandrel fully advanced and the sleeve further everted. In this figure, the obturator has been removed.

FIG. 5a shows the mandrel 110 fully advanced, and the sleeve 102 further everted, shaping the entire surface of the vaginal cavity into the shape of the outer surface of the applicator 100. The applicator now fills the entire vaginal cavity, and the obturator (if used) has been removed from the lumen 112. If the prescription or other factors suggest that the applicator need not or should not be inserted to full depth, the mandrel 110 may be calibrated with markings 111 (FIG. 2) along its length to indicate the depth of insertion into the vagina 122. Such markings would also serve to provide applicators having variable depth capabilities for differing anatomy. FIG. 5a shows the outer surface of the applicator 100 being uniform. It can alternatively be contoured in order to provide other, preferred shapes. Such contours would then result from the additive combination of sleeve and mandrel geometries.

If the contouring sleeve 102 and the mandrel 110 were made to interact in a locking or detent fashion (not shown), this would also serve to prevent the applicator 100 from inadvertently being expelled from the vagina 122. Should it be desirable to provide an external (to the patient) lock between the sleeve 102 and the mandrel 110, a series of radial, blind holes or notches (rather than markings) can be provided along the length of the mandrel, and a conventional pawl or pin (not shown) can be provided on the cuff to engage the holes or notches when proper depth has been attained. Alternatively, a series of laterally extending ridges (not shown) can be provided on each surface, for interaction at a series of eversion positions.

Figure 5B:
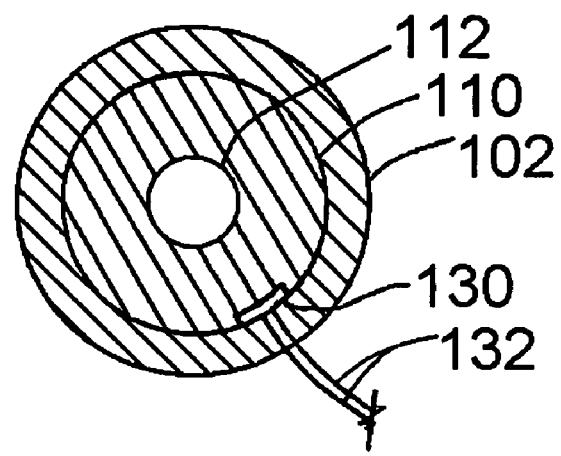
FIG. 5b depicts in transverse section, the apparatus of FIG. 5a at section AA. An optional radiation sensor is shown positioned at the interface between the inverted sleeve and the mandrel.

FIG. 5b is a cross-section view taken at AA in FIG. 5a and shows the everted sleeve 102 juxtaposed against the outer diameter of the mandrel 110. In this embodiment, the outer surface of the mandrel 110 is a circular cylinder, and the wall of the sleeve 102 is uniform, resulting in a circular cross-section of the applicator 100 when the sleeve 102 is everted and held open by the mandrel 110. Note further that the mandrel lumen 112 is shown positioned centrally. In such a circumstance, if a radiation source that emits isotropically, at least in the radial direction transverse to the axis of the mandrel 110, is positioned within the lumen 112, the shape of the transverse isodose traces (concentric loci of points of equal dose intensity) will correspond to the circular shape of the applicator. If different isodose traces are desired, the mandrel lumen may be positioned off-center, or the geometry of the mandrel and sleeve may be varied to produce differently shaped isodose traces in the tissues outside of the applicator. The emission characteristics of the radiation source may also be shaped or shielded, and/or the positioning of the source within the mandrel lumen 112 may be varied to create non-circular isodose shapes as well, or non-symmetrical shapes relative to the vagina. (See copending U.S. patent application Ser. Nos. 11/394,640 and 11/471,277 for descriptions of such methods and apparatus, each of which is hereby referenced and made part of this specification in its entirety.) Rather than sizing the lumen 112 merely to accommodate the radiation source, the lumen may be sized for the additional purpose of venting or evacuating the vaginal space, or for introduction of therapeutic agents as the mandrel is advanced or as radiotherapy progresses. If the lumen 112 is oversize for the source, locator fins (not shown) or other conventional methods of precisely locating the source within the lumen 112 must be provided. In such an embodiment, the proximal end of the mandrel may advantageously further comprise a conventional hub with a central lumen seal (not shown) and a secondary access port from outside the patient to the central lumen for fluid passage. For example, see application Ser. No. 11/481,242, incorporated herein in its entirety. Additional lumina (not shown) may also be provided which communicate with other portions of the applicator to address auxiliary purposes, for example to accommodate wiring for radiation sensors or multiple radiation sources or source positions. FIG. 5b also shows a radiation sensor 130, for example of the MOSFET type, positioned on and fastened to the exterior surface of the mandrel. Such a sensor can communicate to outside the body by conventional wiring 132 (shown schematically), or can communicate information to outside the patient by conventional wireless methods. Alternatively, this sensor or other sensors can be positioned and held in place elsewhere on or within elements of the applicator. The purpose of the sensor (or sensors) is to measure the radiation during radiotherapy. Such sensing can be used to control the therapy and/or to verify that prescribed therapy is being or has been administered. Such control may be by manual adjustment, or may be automated—including in real time during a procedure, to alter or verify absorbed dose during or between fractions. (See copending U.S. patent application Ser. No. 11/394,640 for a description of sensing and feedback control of radiotherapy, said patent application being hereby incorporated herein in its entirety.) Once a radiation source has been characterized by multiple sensor mapping to establish output and stability prior to actual therapy, only a few, or as few as one sensor, is necessary to measure radiation source performance.

Figure 5C:
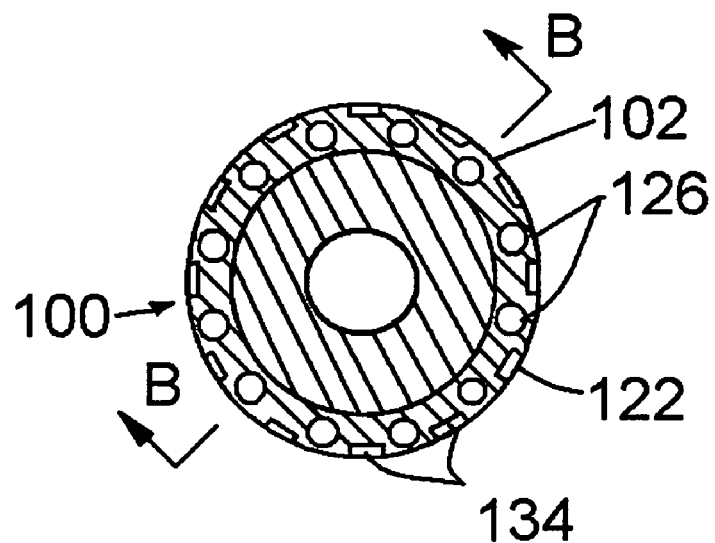
FIG. 5c depicts in transverse section, the apparatus of FIG. 5a at section AA, showing the outer wall of the everted sleeve with a pattern of grooves in the sleeve surface adjacent the vaginal cavity, and optional longitudinal reinforcing fibers in the sleeve wall.

FIG. 5c is a section view of the applicator sleeve 102, again taken at section AA in FIG. 5a. FIG. 5c shows optional grooves 134 in the everted sleeve outer surface for the purpose of facilitating fluid transport between the applicator 100 and the cavity wall 122 of the vagina, such as for the venting of trapped air during placement of the applicator 100 in the vagina, evacuation of seroma, or infusion of therapeutic agents. FIG. 5c also shows optional longitudinal reinforcing members 126 embedded within the wall of the sleeve 102. These may advantageously be flexible cords, for example of braided or stranded polyester, molded within the walls during fabrication. Such reinforcement facilitates further eversion of the sleeve 102 as the mandrel 110 is advanced by preventing stretching of the length of the already everted portion of the sleeve wall. Tension tending to produce such stretching is caused by advancing the mandrel against the resistance provided by the cuff 116. This tension can be reduced by lubrication applied to the sliding surfaces during the eversion process. Such lubrication might for example be a hydrophilic coating applied during applicator fabrication and moistened before insertion into the vagina 122, or glycerin based lubricants such as KY (Johnson & Johnson, New Jersey) applied before vaginal insertion. An example of a hydrophilic surface coating would be LubriLAST (AST Products, Inc., Billerca, Mass.).

The longitudinal cord reinforcing members 126 are useful in resisting tension on mandrel insertion. They will follow the bending or rolling action of the everting sleeve wall as the mandrel 110 is advanced. If the compressive rigidity of the sleeve adjacent to the distal end of the mandrel is insufficient to prevent buckling of the sleeve as the mandrel is advanced, different reinforcing members may be necessary.

Figure 5D:
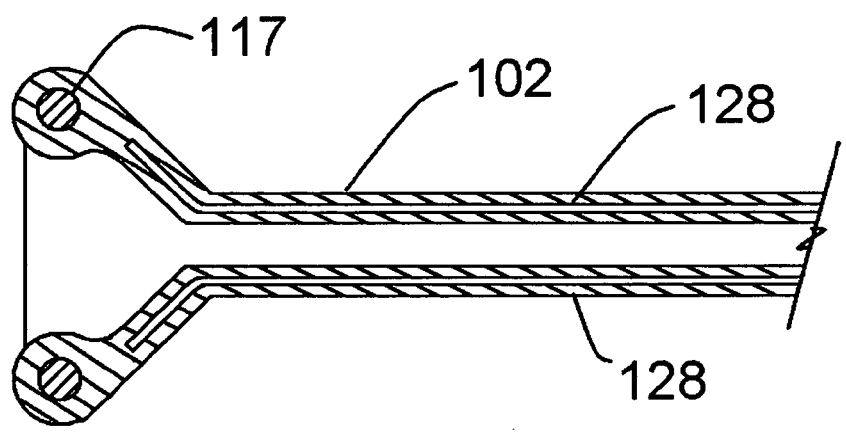
FIG. 5d depicts in longitudinal section view, the distal cuff sleeve wall, but with alternate superelastic Nitinol type of longitudinal reinforcing members having non-uniform thickness along their length.

As shown in FIG. 5d, a potentially useful alternative to cord members, and/or use of an obturator (as described in relation to FIG. 4) are solid reinforcing members 128 made from superelastic Nitinol. Such members provide buckling resistance under axial compression yet form kink-resistant bends on eversion, straightening out easily if not spontaneously when bending forces are removed. Such behavior is exhibited, for example by ZIPWIRE guidewires (Boston Scientific Corp., Natick, Mass. See also U.S. Pat. Nos. 5,597,378 and 6,245,030 for descriptions of this sort of material).

Figure 6:
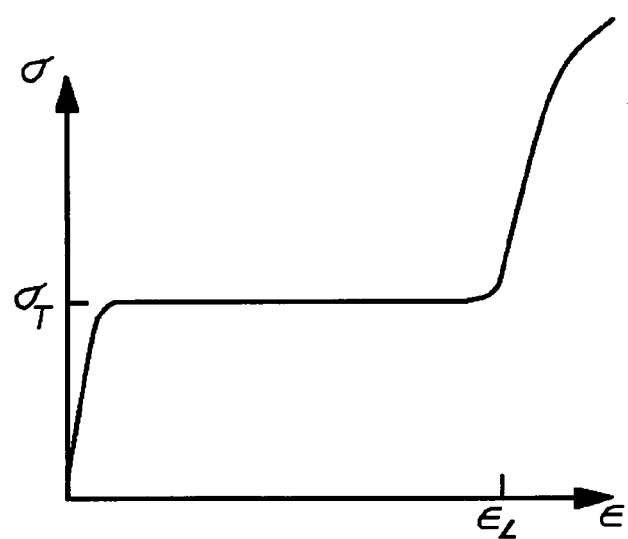
FIG. 6 depicts a stress-strain curve for the alternate superelastic Nitinol type of longitudinal reinforcing members for the applicator sleeve.
Figure 9A:
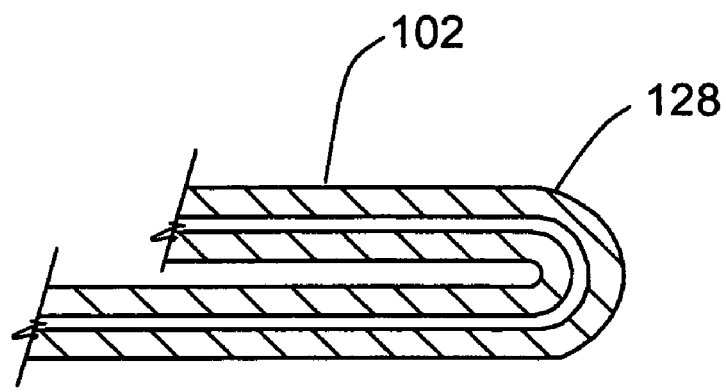
FIG. 9a shows in partial section, the everting sleeve wall at the tightly-curved distal extremity of the applicator when reinforced by a thin section of the alternate type of reinforcing member.
Figure 9B:
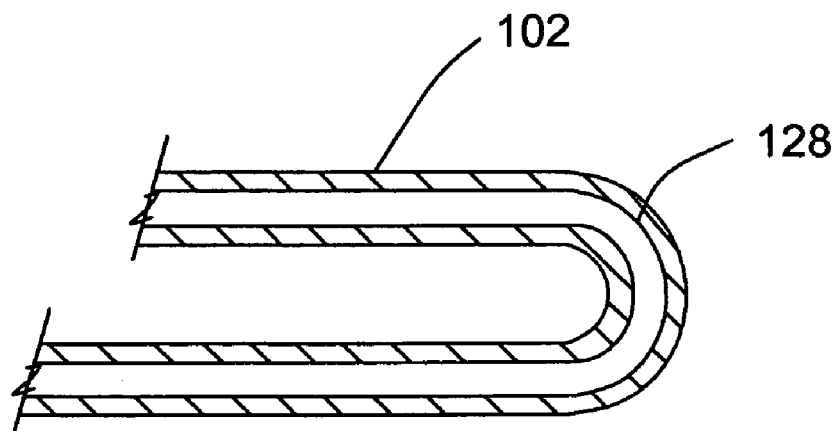
FIG. 9b shows in partial section, the greater radius of the everting sleeve wall when reinforced by a thick section of the alternate type of reinforcing member.

FIG. 6 illustrates the stress-strain characteristics of such superelastic material. Upon loading, stress and strain vary linearly, but at a threshold stress, $\sigma_T$, strain increases greatly without appreciable increase in stress until reaching a strain limit, $\epsilon_L$, whereupon strain will no longer increase without an attendant, significant increase in stress. From the point of this limit strain, $\epsilon_L$, substantially all strain can be recovered upon unloading. This characteristic has important implications in design of the applicator. A reinforcing member 128 exhibiting stress-strain characteristics as in FIG. 6 bends easily until the member's extreme fibers (transverse to the member's neutral axis) reach the limit strain, $\epsilon_L$, which generally happens at one initial point of the bend. In a macro-sense, once $\epsilon_L$ is reached at the one initial point, increased resistance to further bending at that point induces adjacent points along the length of the member to reach $\epsilon_L$ as well. This behavior progresses until at the limit where all portions of the bend reach $\epsilon_L$ concurrently and the shape of the bent member is circular for the entire extent of the bend. The radius of the bent section is proportional to the thickness of the member in the direction transverse to the neutral axis of bending, i.e. in the direction of the radius of curvature. It is therefore clear that, by controlling the thickness of the reinforcing members 128 in the direction described, one may design a sleeve 102 which bends tightly on initial eversion of the distal end 114 of sleeve 102, as shown in FIG. 3 or FIG. 9a, but which will later bend only to a larger but uniform radius more proximally as shown in FIG. 4 or 9b. As is shown in FIG. 4, as eversion progresses, the distal extremity 120 of the applicator 100 progresses into the vaginal cavity, and the bend rolls ahead of the mandrel 110, producing a radially expanding action in keeping with the thickness of the superelastic Nitinol reinforcing members 128. The trailing portion of the wall of the everted sleeve 102 proximal of the distal extremity 120 will straighten and be supported by the mandrel 110. The bending radius of the wall of sleeve 102 when reinforced by various thickness of superelastic members 128 is discussed with respect to FIGS. 9a and 9b below.

Figure 7:
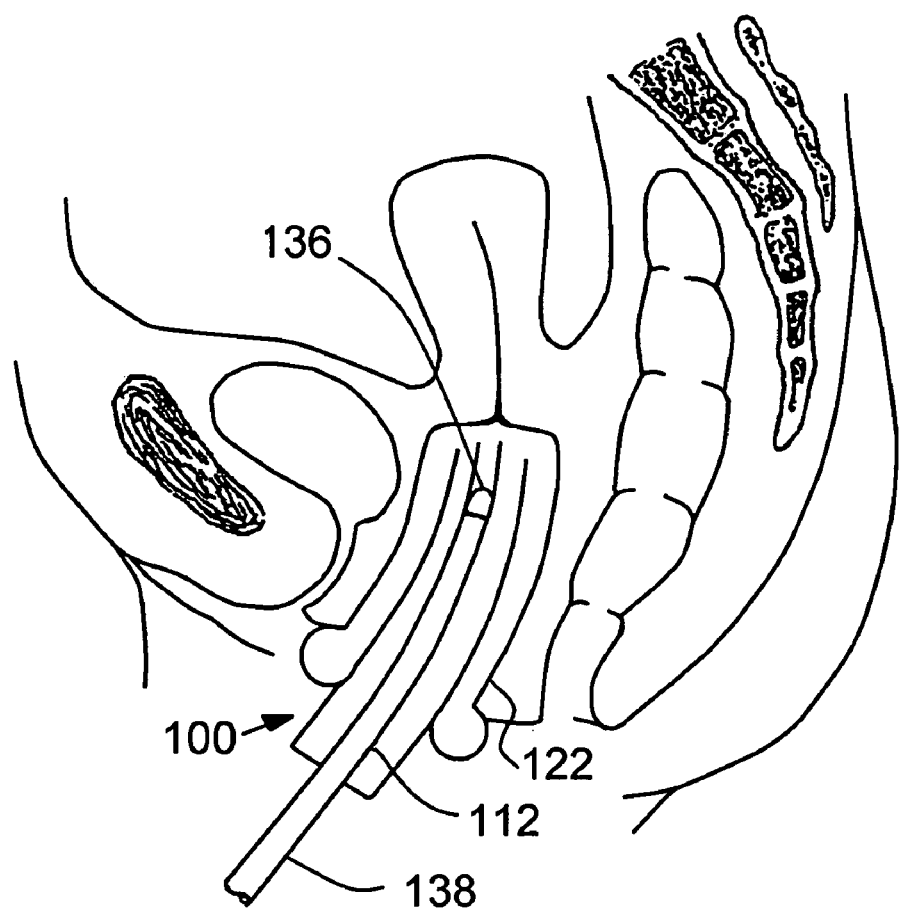
FIG. 7 depicts in sagittal section, the applicator fully deployed in the vagina as in FIG. 5a, and with a radiation source and source catheter positioned within the lumen of the applicator mandrel for delivery of radiation therapy.

FIG. 7 shows in sagittal section, the applicator of FIG. 5a. In this view, the applicator 100 is curved in the medial plane, mimicking the curvature of the anatomy. Use of semi-rigid or flexible mandrel material will permit curved compliance in the manner shown, or alternatively, a more rigid, but curved mandrel can be used to produce the same effect in vagina 122. FIG. 7 also shows a radiation source 136 mounted at the distal end of a source catheter 138, positioned in the lumen 112.

Figure 8:
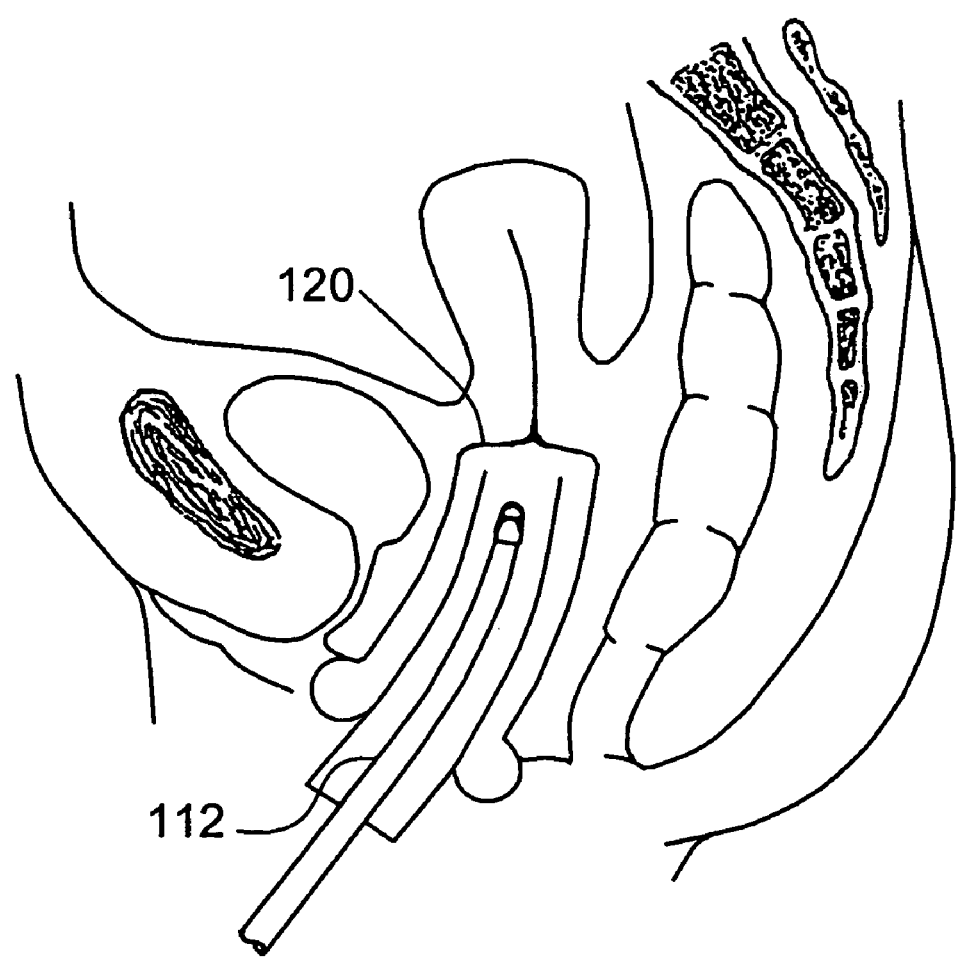
FIG. 8 depicts in section view, a different applicator embodiment of the invention with a closed-end mandrel lumen.

FIG. 8 shows a similar applicator to that shown in FIG. 7, but in this Figure, the mandrel lumen 112 is blind, and does not communicate with the distal end 120 of the applicator.

FIG. 9a depicts a bend which might be formed in the wall of the sleeve 102 during eversion when reinforced by a thin portion of a reinforcing member 128. FIG. 9b depicts a similar section of sleeve wall, but where the thickness of the reinforcing member 128 is thicker, and the radius formed in the everting wall 102 is larger.

In use, the applicator of this invention can be prepared by applying lubrication (by use of KY gel or wetting any hydrophilic coatings) appropriately if it is anticipated that sliding friction between elements of the applicator, or between the applicator and vagina, could be a problem. Next, the distal end of the applicator (sleeve and cuff or handle) are turned inside out if not already everted during manufacture. The distal extremity is next inserted axially into the mouth of the vagina until the cuff (or handle) rests against the patient's anatomy. The mandrel is then advanced into the sleeve until proper depth for therapy is attained (and the locking mechanism, if provided, is properly engaged). If desired, resistance to the mandrel's 110 insertion may be overcome by holding the cuff (or alternate handle) manually if desired to avoid unnecessary pressure on the patient's anatomy.

Auxiliary functions can be connected and provided before, during or after applicator insertion as appropriate for convenience and efficacy. These functions would optionally include sensing, venting, suction, and administration of therapeutic agents as prescribed. Insertion of an isotope source into the applicator from an afterloader or similar device for administering radiation would commence after the applicator is positioned, and any auxiliary functions are enabled. If an electronic x-ray source which can be turned on and off at will is to be used, the source can be positioned at any point in the process as convenient, and switched on when the applicator is properly positioned and auxiliary functions are enabled.

This invention has been described herein in considerable detail in order to instruct one of skill in the art how to practice the invention. It is to be understood, however, that the invention can also be practiced using other methods and apparatus without departing from the scope of the invention itself, as defined in the claims.

We claim:

1. A method for gynecological brachytherapy treatment, comprising:
providing an everting applicator, the applicator comprising a flexible generally tubular sleeve of rubbery elastomeric material having an internal lumen, the sleeve having a sleeve body and distal end wider than the sleeve body and configured to prevent entry into a vagina, the lumen terminating at a distal end opening, a mandrel having an internal mandrel lumen of sufficient size to receive a radiation source inserted into the mandrel lumen and having a distal end connected to a proximal end of the flexible sleeve, and the flexible sleeve having bending flexibility so as to evert when the distal end of the sleeve is braced against or adjacent to the exterior end of a body cavity, placing the distal end of the sleeve at the mouth of a vagina and restraining the distal end while pushing the flexible sleeve to cause the flexible sleeve to evert as it enters and extends into the vagina and restraining the distal end while pushing the flexible sleeve into the vagina, with an inner wall of the sleeve's lumen turning outwardly in progressively unrolling contact against the interior surface of the vagina until the outer surface of the flexible sleeve deeply overlaps the mandrel, and such that the mandrel thus extends at least partially into the vagina surrounded by the everted flexible sleeve, and extending a radiation source from a proximal end of the mandrel into the mandrel lumen to a desired position, and irradiating target tissues of the vagina.

2. The method of claim 1, wherein the mandrel lumen has a closed distal end.

3. The method of claim 1, wherein the mandrel has an open distal end in communication with the lumen of the flexible sleeve.

4. The method of claim 1, further including a radiation sensor generally at the exterior surface of the mandrel, in position to receive radiation from the radiation source in the mandrel lumen, and the method including monitoring radiation received at the sensor during irradiation of target tissues so that dose is monitored and quantified as the irradiation continues.

5. The method of claim 4, further including adjusting the radiation emitted from the radiation source in response to the monitoring of radiation received, as the irradiation continues.

6. The method of claim 4, wherein the radiation sensor is connected wirelessly to an external monitor.

7. The method of claim 4, wherein the radiation sensor is connected by wire to an external monitor.

8. The method of claim 1, wherein the mandrel is of stiffer material than the flexible sleeve.

9. The method of claim 8, wherein the mandrel and flexible sleeve are co-molded and integral.

10. The method of claim 1, wherein the wider distal end comprises an end that diverges to larger diameter and defines an open end larger than the lumen in the sleeve body.

11. The method of claim 10, wherein the larger-diameter open end of the tubular sleeve includes a cuff at which full thickness of the sleeve is increased.

12. The method of claim 1, wherein the flexible sleeve includes grooves on a sleeve surface which becomes an everted outer surface, including grooves in the sleeve surface and the method including directing fluid outwardly along the grooves during the irradiation procedure.

13. The method of claim 1, wherein the flexible sleeve includes grooves on a sleeve surface which becomes an everted outer surface, including grooves in the sleeve surface and the method including delivering liquid therapeutic agents into the vagina to the target tissues along the grooves.

* * * * *